Figure 1:
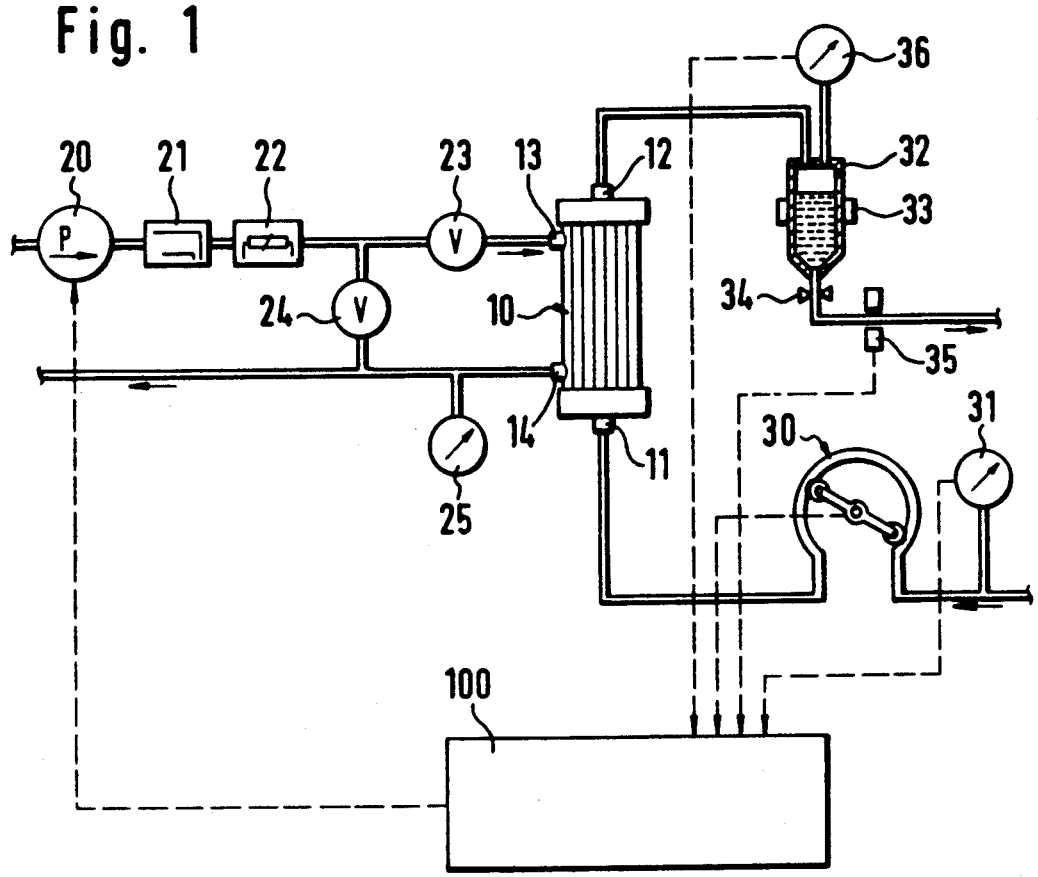

United States Patent [19]

Polaschegg

[11] Patent Number: 5,092,836
[45] Date of Patent: Mar. 3, 1992

[54] HEMODIALYSIS APPARATUS WITH AUTOMATIC ADJUSTMENT OF DIALYSIS SOLUTION FLOW

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 495,363

[22] Filed: Mar. 19, 1990

[30] Foreign Application Priority Data

Mar. 25, 1989 [DE] Fed. Rep. of Germany ....... 3909967

[51] Int. Cl.⁵ .............................................. A61M 5/00
[52] U.S. Cl. ........................................ 604/4; 604/5; 604/6; 210/87; 210/646
[58] Field of Search ...................... 604/4–6; 210/646, 85, 97, 149, 181, 321.65, 321.72, 650, 742

[56] References Cited

U.S. PATENT DOCUMENTS

| | | | |
|---|---|---|---|
| 4,353,368 | 10/1982 | Slovak et al. | 604/4 |
| 4,650,458 | 3/1987 | Dahlberg et al. | 604/5 |
| 4,776,837 | 10/1988 | Kopp | 604/4 |
| 4,828,543 | 5/1989 | Weiss et al. | 604/4 |
| 4,885,001 | 12/1989 | Leppert | 604/4 |
| 4,894,164 | 1/1990 | Polaschegg | 604/5 X |
| 4,923,598 | 5/1990 | Schäl | 604/5 X |

Primary Examiner—Robert A. Hafer
Assistant Examiner—Kerry Owens
Attorney, Agent, or Firm—Jack Schuman

[57] ABSTRACT

The invention concerns a hemodialysis apparatus with a hemodialyser (10), which on the blood side has a blood pump (30) to convey blood from a patient to the dialyser (10) and on the dialysis solution side has a dialysis solution pump (20) to convey dialysis solution to the dialyser. The hemodialysis apparatus has a control device (100) whereby a signal derived from the magnitude of the blood flow is fed to the said device on the input side and whereby the said device gives a signal on the output side as a function of the blood flow in order to adjust the dialysis solution flow. With an automatic control device of this type dialysis concentrate, prepared water and energy can be saved. The predetermined control function can be a linear function. It can also be given in the form of numerical data which is fed into a matrix in the control device (100) which for every blood flow of one particular dialyser (10) gives a dialysis solution flow at which a certain percentage of clearance is achieved when the dialysis solution flow is continuous.

13 Claims, 1 Drawing Sheet

HEMODIALYSIS APPARATUS WITH AUTOMATIC ADJUSTMENT OF DIALYSIS SOLUTION FLOW

The invention concerns a hemodialysis apparatus comprising a hemodialyser which has on the blood side a blood pump to convey the blood from a patient to the dialyser and on the dialysis solution side a dialysis solution pump to convey the dialysis solution to the dialyser.

Similar hemodialysis apparatuses are known in a variety of forms, e.g. in DE-PS 36 36 995.

Traditionally these hemodialysis apparatuses are operated with a constant dialysis solution flow rate of 500 ml/min which cannot be changed by the user. More recent apparatuses allow a graded, manual adjustment in order to employ other dialysis solution flow rates such as, for example, 300, 500 and 800 ml/min. Higher dialysis solution flow rates are especially necessary to achieve a high clearance when there are high blood flows of 400 ml/min or more.

The cost of dialysis treatment with such hemodialysis apparatuses is made up of the following:
 fixed costs for the treatment ward and the dialysis apparatus (depreciation and repairs),
 costs of materials used: dialyser, blood pump system, drain tubes, swabs, disinfectant, dialysis concentrate, prepared water and energy costs,
 personnel costs.

With this type of dialysis apparatus the above-mentioned fixed and personnel costs do not allow much room for manoeuver in the attempt to keep the treatment costs as low as possible. The costs of materials used is an area where a saving could be made.

It is well known (see J. E. Sidgell, B. Tersteegen, Artificial Organs, 10 (3) pages 219-225, 1986) that in the widely used capillary dialysers with a blood flow: dialysis solution flow ratio of 1:2 and only a negligibly small reduction in the clearance occurs in contrast with the above-mentioned "standard conditions" with a dialysis solution flow of 500 ml/min. Although this effect has been known for a long time and can also be seen in the specifications of dialyser manufacturers and, moreover, although the pressure of costs has been well documented, especially in the USA, leading to the, re-use of products which had been designed as disposable articles, there have, however, been no measures taken towards saving dialysis concentrate, water and energy since a manual adjustment of the dialysis solution flow rate in many cases is not possible, is also too troublesome, according to the experts, and involves the danger of operational error.

The invention has the object of designing a dialysis apparatus as described at the beginning of the specification in such a way that the consumption of the dialysis concentrate, prepared water and energy is minimized in order to reduce the cost of a dialysis treatment without impairing the quality of the treatment.

According to the invention the solution to the problem lies in the fact that a control device is provided whereby a signal derived from the rate of the blood flow is fed to the said device on the input side and the said device gives a signal as a function of the blood flow on the output side in order to adjust the dialysis solution flow.

With the help of the automatic control device of the invention the dialysis solution flow in the hemodialysis is always automatically adjusted as a function of the blood flow. In this way it is advantageously assured that at any time during the hemodialysis treatment, including the preparation and final phases, a dialysis solution flow sufficient for the treatment, but at the same time not too high, is automatically adjusted. The dialysis apparatus fitted with the automatic control device of this invention is of advantage because of the low operational costs.

It is well known that in hemodialysis apparatuses of the type mentioned at the beginning the usual sensors and control elements are connected to a computer which controls or regulates the process automatically. The control device of the dialysis solution flow as a function of the blood flow is not foreseen in the known cases nor is there any indication to this end.

The invention or rather the characteristic features of the invention are described in more detail by means of an example shown in the drawing.

Figure 2:
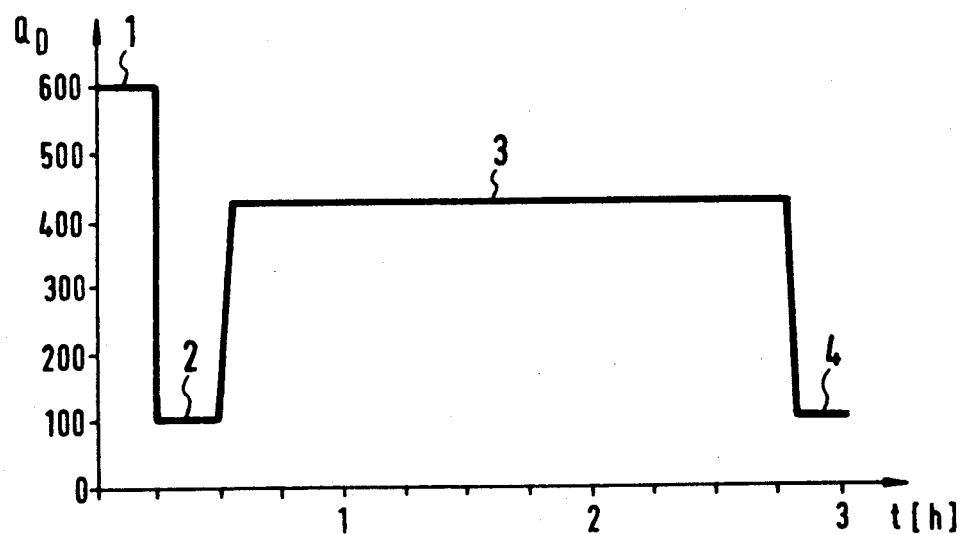

It shows:

FIG. 1 a block diagram of a customary hemodialysis apparatus with the control device of this invention, FIG. 2 an embodiment of the control function of the control device in this invention with linear sections.

FIG. 1 shows a conventional hemodialysis apparatus comprising a dialyser (10) which has an inlet (11) and an outlet (12) on the blood side and an inlet (13) and an outlet (14) on the dialysis solution side. A dialysis solution pump (20) to convey dialysis solution from a dialysis solution source, which is not described in any more detail, is provided in the dialysis solution cycle.

The dialysis solution cycle has a customary conductivity sensor (21) and a temperature sensor (22). Furthermore, a dialyser valve 29 is provided with which the dialysis solution can be diverted into the dialyser (10). The dialysis solution can be taken away from the dialyser by means of a bypass valve (24). The dialysis solution cycle also has a pressure sensor (25) to measure the pressure of the dialysis solution downstream from the dialyser.

In the blood line circuit there is a blood pump (30) which conveys blood from a patient (not shown) to the dialyser. Upstream from the blood pump (30) there is an arterial pressure sensor (31). In the blood line circuit downstream from the dialyser (10) there is also a venous bubble trap (32) at which an air detector (33) enables the detection of air and blood foam.

Downstream from the bubble trap (32) there is a venous shut-off device (34) used to shut off the external circulation from the patient in the event of a dangerous situation arising. In the blood line system there is furthermore arranged an optical detector (35) which can differentiate between the saline solution and blood in the tube downstream from the venous bubble trap (32), and a venous return pressure detector (36), which is connected to the bubble trap(32).

The self-actuating control circuit of the invention is contained in the control device (100). A signal, derived from the magnitude of the blood flow rate, is fed into this control device on the input side. This signal is accordingly derived from the pumping rate set for the blood pump (30) which itself, for example, is derived from the rotational speed of the blood pump (30). The dialysis solution flow is adjusted automatically on the basis of the output signal of the control circuit. For this purpose the output of the control circuit (100) is connected to the dialysis solution pump (20), or to be more exact to the input of the control circuit for the adjustment of the pumping rate of this pump. The control device (100) also incorporates further devices which can identify which of the conditions 1 to 4 according to FIG. 2 the hemodialysis device is in. These conditions 1 to 4 will be explained in more detail later in connection with FIG. 2. For this purpose the output signals of the arterial pressure detector (31), the venous pressure detector (36) and the optical detector (35) are connected to the input of the control device, as shown in the signal path indicated by a broken line.

In addition to the control circuit of the invention the control device (100) may also incorporate a normal control unit to control and monitor the hemodialysis. In this case all the other elements drawn in FIG. 1 should be thought of as connected to the control device (100) by a signal path.

The control device (100) is so constructed and regulated that the output signal of the automatic control which regulates the dialysis solution flow is a predetermined function of the input signal derived from the blood flow. This function is derived according to predetermined criteria from the area of clearance performance (clearance as a function of dialysis solution flow and blood flow). In the simplest case this predetermined function is a linear one. It can also be given in the form of a polynomial or by numerical data fed into in a matrix in the control circuit which, for every blood flow of one dialyser, gives the dialysis solution flow at which a certain percentage of the clearance (e.g. 95%) is reached, when the dialysis solution flow is infinite. In this case the control function is stored in a so-called table.

The control function controlling the dialysis solution flow $Q_D$ incorporated in the control device (100) may consist of several chronological sections. These sections are represented symbolically in FIG. 2. In the first section a re-utilised dialyser filled with disinfectant is completely cleaned by dialysis. On the blood side a saline solution recirculates at a higher speed. The dialysis solution side is operated at maximum speed (e.g. 800 ml/min).

In the second section the hemodialysis apparatus is connected to the patient. The dialysis solution flow is set at at a constant low value to prevent the extracorporeal circuit from cooling down too much.

In the third section the actual dialysis itself takes place. The dialysis solution flow $Q_D$ is controlled as a function of the blood flow $Q_B$ according to the general function $Q_D = f(Q_B)$.

In the fourth section the dialysis is completed. The dialysis solution flow is set to a constant value which is maintained in the stand-by status until the next treatment or the next step in the procedure.

The condition (section) of the dialysis can be automatically identified on the basis of the following signals.

Condition 1: In order to effect a clear rinse of the dialyser the operator sets the blood pump (30) to a high speed (normally 400 ml/min). The optical detector (35) indicates the signal "light", i.e., the presence of saline solution in the tube system. The pressure in the arterial pressure detector is $>-50$ mmHg, whereas the pressure in the venous return pressure detector is $<50$ mmHg. The latter pressure values are typical, but may change depending on the type of tubes used or the rinsing method. They can, however, be determined at short intervals after one in-vitro trial. As occasionally foam builds up in the bubble trap (32) during the rinsing, this signal can also be used as a safety check for the air detector.

Condition 2: When the patient is connected to the apparatus the pumping rate of the blood pump (30) at the end of condition 1 is set to 0 and slowly increased. The optical detector (35) still shows the signal "light".

Condition 3: During the dialysis the optical detector (35) shows the signal "dark" to indicate the presence of blood.

Condition 4: The blood pump (30) is set to 0 at the end of condition 3 and the pumping rate is set to a low value. The optical detector shows the signal "dark".

Since the heat energy balance of the patient is dependent on the heat energy fed or withdrawn from him by the dialyser and this in turn is determined by the amount and temperature of the dialysis solution, the control circuit of the invention is appropriately extended to include a device to control the dialysis solution and the temperature, dependent on the flow.

Normally the dialysis solution temperature is measured and regulated inside the dialysis apparatus, but when measured at this point energy is released outside and therefore the temperature set for the dialysis solution differs from that at the dialyser input point (13). A temperature regulation independent of the dialysis solution flow will therefore assume the general form:

$$T_{Control} = g(T_{set}, Q_D, Q_B).$$

($T_{set}$ = set value of temperature T)

Since the dialysis solution flow $Q_D$ is regulated as a function of the blood flow, this general rule can be transformed into:

$$T_{Control} = g(T_{set}, Q_B)$$

($T_{Control}$ = temperature value to be regulated)

With this correlation the energy transfer is kept constant independent of any changes in the dialysis solution flow. It is not necessary to regulate according to this correlation if the energy transfer is measured directly in the external circulation upstream and downstream from the dialyser (10).

A simple regulation of the energy transfer in the dialyser (10) is also possible if the temperature is measured in the dialysis solution circuit upstream and downstream from the dialyser (10).

In the simplest case the function $Q_D = f(Q_B)$ will become:

$$Q_D = a \text{ for } Q_B > = 0 \text{ and} < = 100 \text{ ml/min}$$

and $$Q_D = b \cdot Q_B \text{ for } 100 \text{ ml/min}$$

whereby a is set such that the extracorporeal circuit does not cool down greatly (at a normal blood flow rate of approx. 50–100 ml/min) and b is selected according to the characteristics of the dialyser.

I claim:

1. Hemodialysis apparatus adapted to receive from a patient in need of hemodialysis blood to be treated and to return treated blood to the patient, said hemodialysis apparatus comprising:

(a) a hemodialyzer having a blood side and a dialysis solution side,
(b) blood pumping means for conveying blood from the patient through the blood side of said hemodialyzer,
(c) dialysis solution pumping means for conveying dialysis solution through the dialysis side of said hemodialyzer,
(d) first control means having an input and an output,
(e) first means responsive to the volumetric rate of output of said blood pumping means for feeding into the input of said first control means an input signal which is a function of the volumetric rate of output of said blood pumping means,
(f) said first control means for generating at its output an output signal which is a predetermined function of the volumetric rate of output of said blood pumping means,
(g) second control means operatively connected to said dialysis solution pumping means for controlling the volumetric rate of output of said dialysis solution pumping means in response to signals communicated to said second control means,
(h) second means operatively interposed between the output of said first control means and said second control means for communicating to said second control means the out put signal generated at the output of said first control means,
(i) whereby to adjust the volumetric rate of output of said dialysis solution pumping means according to the predetermined function of the volumetric rate of output of said blood pumping means.

2. Hemodialysis apparatus as in claim 1, wherein said predetermined function is linear.

3. Hemodialysis apparatus as in claim 1, wherein said predetermined function is polynomial.

4. Hemodialysis apparatus as in claim 1, wherein said predetermined function is given in the form of numerical data which, for every volumetric rate of flow of blood for one dialysis, provides the volumetric rate of flow of dialysis solution required to attain a specific degree of blood purification.

5. Hemodialysis apparatus as in claim 1, wherein said second control means comprises a microprocessor.

6. Hemodialysis apparatus as in claim 1, further comprising:
(j) third means adapted to determine the temperature of said dialysis solution and to communicate to said second control means a control signal which is a function of said temperature,
(k) whereby to supplement the adjustment of the volumetric rate of output of said dialysis solution pumping means recited in (i).

7. Hemodialysis apparatus as in claim 6, wherein said third means comprises a first temperature sensoror upstream of the hemodialyzer and a second temperature sensor downstream of the hemodialyzer.

8. Method of treating the blood of a patient in need of hemodialysis in a hemodialyzer having a blood side and a dialysis solution side, blood pumping means adapted to convey blood from the patient through the blood side of the hemodialyzer and dialysis solution pumping means adapted to convey dialysis solution through the dialysis solution side of the hemodialyzer, said method comprising:
(a) sensing the volumetric rate of output of the blood pumping means,
(b) generating a first signal which is a function of the volumetric rate of output of said blood pumping means,
(c) generating a second signal which is a predetermined function of said first signal,
(d) employing said second signal to control the volumetric rate of output of said dialysis solution pumping means,
(e) whereby adjust the volumetric rate of output of said dialysis solution pumping means in accordance with said predetermined function.

9. Method as in claim 8, wherein said predetermined function is linear.

10. Method as in claim 8, wherein said predetermined function is polynomial.

11. Method as in claim 8, wherein said predetermined function is provided in the form of numerical data which, for every volumetric rate of flow of blood for one dialysis, provides the volumetric rate of flow of dialysis solution required to attain a specific degree of blood purification.

12. Method s in claim 8, further comprising:
(f) determining the temperature of said dialysis solution,
(g) generating a third signal which is a function of said temperature,
(h) employing said third signal to supplement the control of said dialysis solution pumping means.

13. Method as in claim 8, further comprising:
(f) determining the temperature of said dialysis solution upstream of said hemodialyzer,
(g) determining the temperature of said dialysis solution downstream of said hemodialyzer,
(h) generating a third signal which is a function of said temperatures,
(i) employing said third signal to supplement the control of said dialysis solution pumping means.

* * * * *

UNITED STATES PATENT AND TRADEMARK OFFICE
CERTIFICATE OF CORRECTION

PATENT NO. : 5,092,836

DATED : March 3, 1992

INVENTOR(S) : Hans-Dietrich Polaschegg

It is certified that error appears in the above-identified patent and that said Letters Patent is hereby corrected as shown below:

Column 2, line 34, after "dialyser valve," delete "29" and substitute therefor --23--.

Column 6, line 1, after "Method" delete "s" and substitute therefor --as--.

Signed and Sealed this

Twenty-fifth Day of May, 1993

Attest:

MICHAEL K. KIRK

*Attesting Officer*     Acting Commissioner of Patents and Trademarks